April 4, 1961 F. W. ANDERSON Plant Pat. 2,044

NECTARINE TREE

Filed July 5, 1960

WITNESS

Addison E. Avery

INVENTOR

Frederic W. Anderson

Webster & Webster

ATTYS.

United States Patent Office

Plant Pat. 2,044
Patented Apr. 4, 1961

2,044

NECTARINE TREE

Frederic W. Anderson, Merced, Calif., assignor to Kim Bros. a copartnership doing business under the fictitious name and style of Reedley Nursery, Reedley, Calif.

Filed July 5, 1960, Ser. No. 40,982

1 Claim. (Cl. 47—62)

This invention relates to a new and distinct variety of nectarine tree which bears yellow-fleshed freestone fruit characterized—as to novelty—by ripening earlier than the present commercial varieties; the ripening period being approximately one week earlier than the Grand River (United States Plant Patent No. 1,248) and the Merrill Sunrise (United States Plant Patent No. 1,256), and approximately two weeks earlier than the John Rivers (unpatented).

The present variety of nectarine tree is further characterized—as to novelty—by fruit whose skin is smoother than the above named varieties, and—when the fruit is ripe—by an attractive exterior red color shading to maroon which almost entirely overspreads a yellow ground color. This color characteristic is in contrast to the striped color of such other varieties.

The herein claimed variety of nectarine tree was originated by me in my experimental orchard located near Merced, California, as a second generation seedling of a cross between the Le Grand nectarine (United States Plant Patent No. 549) and the July Elberta peach (United States Plant Patent No. 30).

After I originated the variety it was maintained by me under careful and continuing observation, and at its maturity I recognized its distinct and desirable characteristics described above and selected the variety for reproduction.

Asexual reproduction of the variety was accomplished by me, in my experimental orchard as aforesaid, by topworking on mature nectarine trees; such reproductions having run true in all respects.

Figure 1:
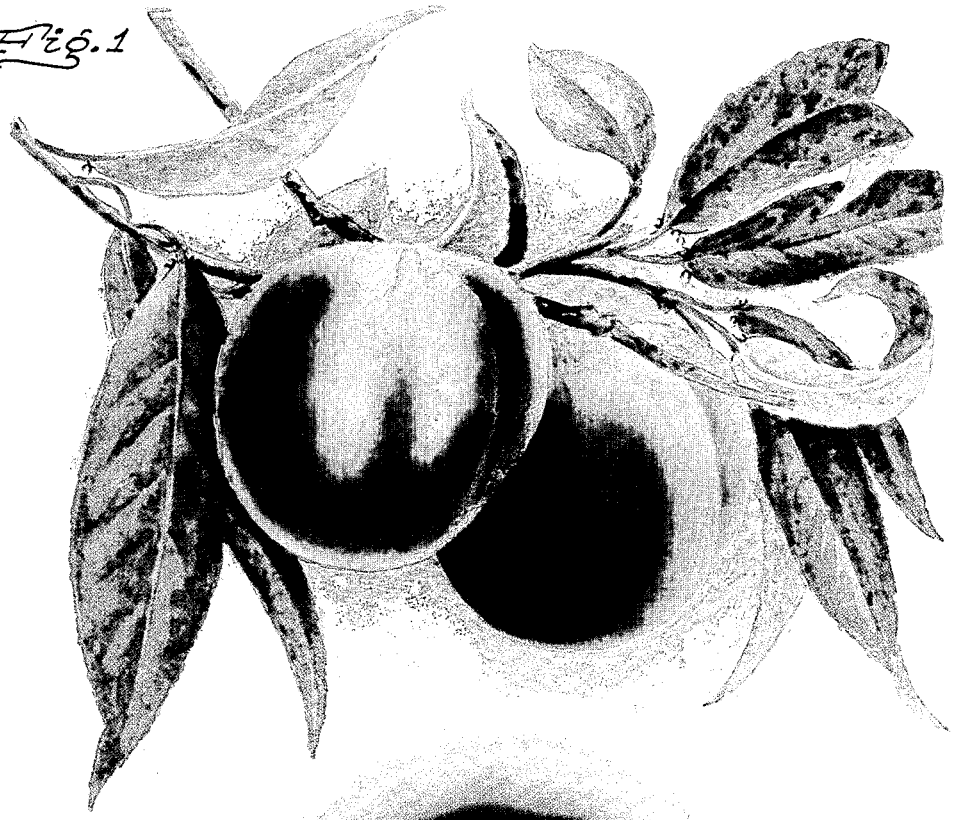
Fig. 1 is an elevation showing two of the nectarines, together with twigs and leaves.
Figure 2:
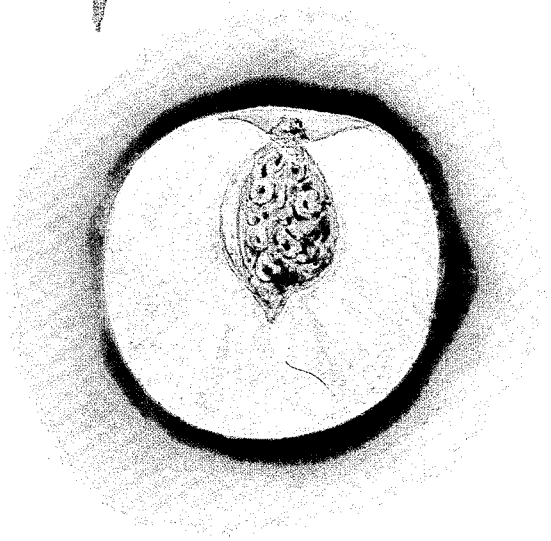
Fig. 2 is a sectional elevation of one of the nectarines with the stone remaining in place.

Referring to pomological details of this new and distinct variety of nectarine tree and its fruit, the following is an outline description thereof; all major color plate identifications being by reference to Maerz and Paul Dictionary of Color.

Tree:
- *Size.*—Large.
- *Vigor.*—Vigorous.
- *Form.*—Spreading.
- *Production.*—Very productive.
- *Bearing.*—Regular bearer.

Trunk: Size—stocky to medium.

Branches: Size—stocky to medium.

Leaves:
- *Size.*—Large to medium.
- *Texture.*—Smooth.
- *Margin.*—Crenate.
- *Petiole.*—Medium length.
- *Glands.*—Average number and position—usually two on petiole and one to three on blade. Medium size; reniform; no stipules.
- *Color.*—Top side—medium green (22–L–8 to 22–L–9). Under side—lighter green (21–J–5).

Flower buds:
- *Size.*—Medium.
- *Length.*—Medium.

Flowers:
- *Blooming period.*—March 8 to March 20, 1959; approximately with the Elberta peach.
- *Size.*—Large.

Fruit:
- *Maturity when described.*—June 12, 1959.
- *Date of first picking.*—June 5, 1959.
- *Date of last picking.*—June 12, 1959.
- *Size.*—Uniform; large to medium. Average diameter axially—2¼". Average transversely in suture plane—2¼".
- *Form.*—Uniform; globose.
- *Suture.*—Distinct; extends from base to apex, with slight depression beyond pistil point.
- *Ventral surface.*—Rounded slightly.
- *Cavity.*—Elongated in suture plane, with suture showing on both sides.
- *Apex.*—Short.

Skin:
- *Thickness.*—Thick to medium.
- *Texture.*—Tough to medium; smooth.
- *Tendency to crack.*—None in wet season.
- *Down.*—Wanting.
- *Color.*—Yellow ground color (11–K–6) almost entirely overspread with red (4–L–6 to 6–L–6), shading to maroon (7–L–6).

Flesh:
- *Juice.*—Moderate.
- *Texture.*—Firm; crisp; meaty.
- *Ripens.*—Even.
- *Flavor.*—Subacid.
- *Aroma.*—Very little.
- *Eating quality.*—Good.
- *Color.*—Yellow (10–L–6 shading to 11–L–8).

Stone:
- *Type.*—Free when ripe.
- *Size.*—Medium. Average length—1¼". Average breadth—⅞". Average thickness—⅝".
- *Form.*—Ovoid.
- *Base.*—Straight.
- *Apex.*—Acute.
- *Sides.*—Equal.
- *Surface.*—Pitted throughout.
- *Ridges.*—Rounded.
- *Pits.*—Angular.
- *Dorsal edge.*—Full, with broad groove to above center.
- *Tendency to split.*—Slight.
- *Color.*—Light brown (12–K–8 shading to 13–L–11).

Use: Market; dessert.

Keeping quality: Good.

Shipping quality: Good.

The tree and its fruit herein described may vary in slight detail due to climatic and soil conditions under which this variety may be grown; the present description being of the variety as grown in the Central Valley of California.

The following is claimed:

A new and distinct variety of nectarine tree, as illustrated and described, which bears globose, large to medium, freestone fruit having yellow flesh; characterized by a ripening period approximately one week earlier than the Grand River and Merrill Sunrise nectarines and approximately two weeks earlier than the John Rivers nectarine; and further characterized—in comparison with said other varieties—by smoother skin, and—when ripe—by an exterior red color shading to maroon which almost entirely overspreads a yellow ground color.

No references cited.